(12) United States Patent
Toledano

(10) Patent No.: US 8,983,171 B2
(45) Date of Patent: Mar. 17, 2015

(54) SYSTEM AND METHOD FOR INSPECTING STRUCTURES FORMED OF COMPOSITE MATERIALS DURING THE FABRICATION THEREOF

(71) Applicant: Israel Aerospace Industries Ltd., Ben-Gurion Airport (IL)

(72) Inventor: Ilan Toledano, Tel Aviv (IL)

(73) Assignee: Israel Aerospace Industries Ltd., Lod (IL)

( * ) Notice: Subject to any disclaimer, the term of this patent is extended or adjusted under 35 U.S.C. 154(b) by 118 days.

(21) Appl. No.: 13/727,196

(22) Filed: Dec. 26, 2012

(65) Prior Publication Data

US 2014/0177936 A1 Jun. 26, 2014

(51) Int. Cl.
| | |
|---|---|
| *G06T 7/00* | (2006.01) |
| *G01N 21/88* | (2006.01) |
| *B29C 70/38* | (2006.01) |
| *G01N 21/95* | (2006.01) |
| *B29C 70/54* | (2006.01) |
| *G01N 21/84* | (2006.01) |

(52) U.S. Cl.
CPC .............. *G06T 7/0004* (2013.01); *B29C 70/38* (2013.01); *B29C 70/386* (2013.01); *G01N 21/88* (2013.01); *G01N 21/95* (2013.01); *B29C 70/541* (2013.01); *G01N 2021/8472* (2013.01)
USPC ...................................................... 382/141

(58) Field of Classification Search
None
See application file for complete search history.

(56) References Cited

U.S. PATENT DOCUMENTS

| | | | |
|---|---|---|---|
| 3,853,756 A | 12/1974 | Stana | |
| 4,591,400 A | 5/1986 | Fradenburgh | |
| 4,693,678 A | 9/1987 | Von Volkli | |
| 4,780,262 A | 10/1988 | VonVolkli | |
| 5,016,895 A | 5/1991 | Hollingsworth | |
| 5,059,377 A | 10/1991 | Ashton | |
| 5,087,187 A | 2/1992 | Simkulak | |
| 5,332,178 A | 7/1994 | Williams | |
| 5,419,554 A | 5/1995 | Krone | |
| 5,454,895 A | 10/1995 | Imparato | |
| 5,772,950 A | 6/1998 | Brustad | |
| 5,963,660 A | 10/1999 | Koontz | |
| 6,041,132 A * | 3/2000 | Isaacs et al. | .................. 382/100 |
| 6,112,617 A | 9/2000 | Abrams | |

(Continued)

FOREIGN PATENT DOCUMENTS

WO 2013/005206 1/2013

OTHER PUBLICATIONS

An International Search Report and a Written Opinion both dated Oct. 5, 2012, which issued during the prosecution of Applicant's PCT/IL12/00226.

(Continued)

*Primary Examiner* — Jon Chang
(74) *Attorney, Agent, or Firm* — Sughrue Mion, PLLC

(57) ABSTRACT

A method for inspecting structures formed of composite materials during the fabrication thereof including imaging multiple individual plies of a structure, whereby the locations and orientations of edge joints between adjacent courses of each ply are recorded, ascertaining mutual offsets in the locations of mutually parallel ones of the edge joints in the multiple individual plies and providing an output indication when at least one mutual offset of the edge joints is less than a predetermined minimum offset.

18 Claims, 5 Drawing Sheets

(56) References Cited

U.S. PATENT DOCUMENTS

| | | |
|---|---|---|
| 6,319,346 B1 | 11/2001 | Clark |
| 6,561,459 B2 | 5/2003 | Amaoka |
| 6,630,221 B1 | 10/2003 | Wong |
| 6,743,504 B1 | 6/2004 | Allen |
| 6,871,684 B2 | 3/2005 | Engelbart |
| 6,896,841 B2 | 5/2005 | Velicki |
| 7,555,404 B2 | 6/2009 | Brennan |
| 7,563,375 B2 | 7/2009 | Liberman |
| 7,676,923 B2 | 3/2010 | Maille |
| 7,681,835 B2 | 3/2010 | Simpson |
| 7,889,907 B2 | 2/2011 | Engelbart |
| 8,068,659 B2 | 11/2011 | Engelbart |
| 2004/0031567 A1 | 2/2004 | Engelbart |
| 2005/0047643 A1* | 3/2005 | Lowe ............................ 382/141 |
| 2005/0151007 A1 | 7/2005 | Cadogan |
| 2005/0276466 A1* | 12/2005 | Vaccaro et al. ............... 382/152 |
| 2006/0249626 A1 | 11/2006 | Simpson |
| 2007/0034313 A1 | 2/2007 | Engelbart |
| 2007/0173966 A1 | 7/2007 | Oldani |
| 2007/0229805 A1 | 10/2007 | Engelbart et al. |
| 2008/0281554 A1* | 11/2008 | Cork et al. .................... 702/150 |
| 2009/0039566 A1 | 2/2009 | Rodman |
| 2009/0043533 A1 | 2/2009 | Brennan |
| 2009/0072090 A1 | 3/2009 | Kallinen |
| 2009/0169056 A1* | 7/2009 | Engelbart et al. ............. 382/106 |
| 2010/0166988 A1 | 7/2010 | Defoort |
| 2010/0204815 A1 | 8/2010 | Murrish et al. |
| 2010/0213644 A1 | 8/2010 | Driver |
| 2011/0003163 A1 | 1/2011 | Wood |
| 2011/0168324 A1 | 7/2011 | Ender |
| 2011/0274369 A1* | 11/2011 | Smith et al. ................... 382/280 |
| 2012/0147175 A1* | 6/2012 | Kawaguchi et al. ........... 348/88 |
| 2013/0011605 A1 | 1/2013 | Miller |

OTHER PUBLICATIONS

European Search Report dated Apr. 17, 2014, which issued during the prosecution of Applicant's European App No. 13 19 6385.

* cited by examiner

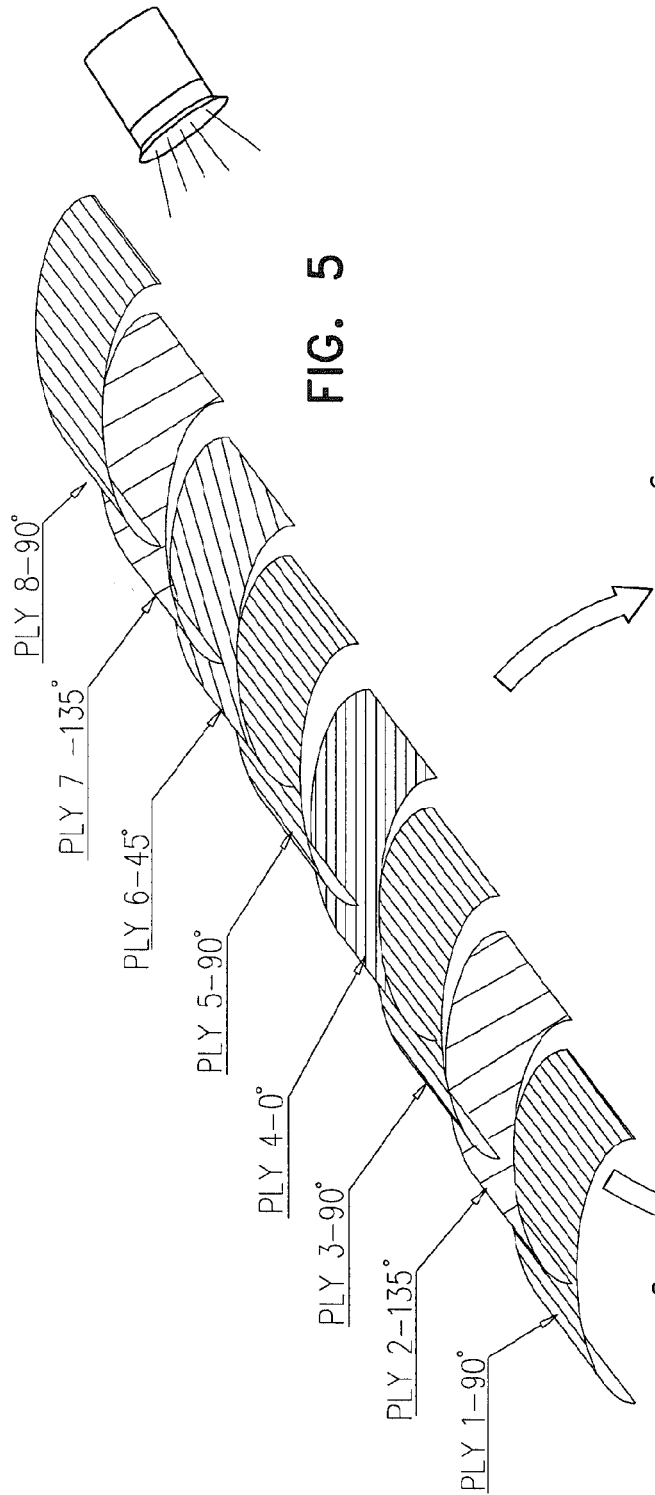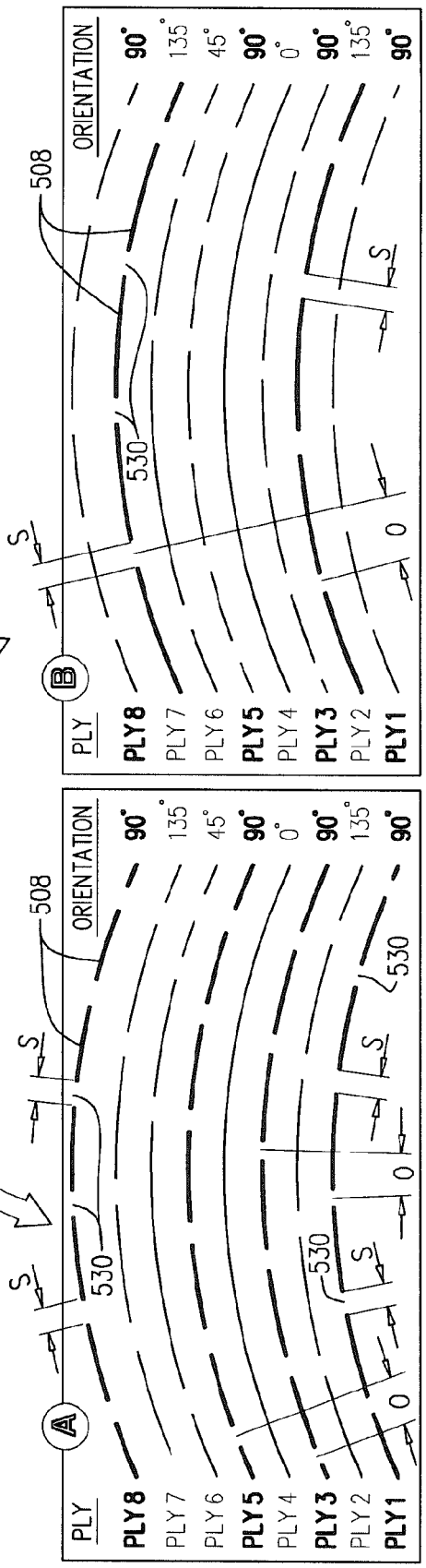
FIG. 5

SYSTEM AND METHOD FOR INSPECTING STRUCTURES FORMED OF COMPOSITE MATERIALS DURING THE FABRICATION THEREOF

FIELD OF THE INVENTION

The present invention relates generally to the fabrication of structures from composite materials.

BACKGROUND OF THE INVENTION

The following publications are believed to represent the current state of the art:
U.S. Pat. Nos.: 8,068,659; 7,889,907 and 5,963,660; and
U.S. Published Patent Application Nos.: 2009/0043533; 2007/0173966; 2007/0034313 and 2004/0031567.

SUMMARY OF THE INVENTION

The present invention seeks to provide a system and methodology for inspecting structures formed of composite materials during the fabrication thereof.

There is thus provided in accordance with a preferred embodiment of the present invention a method for inspecting structures formed of composite materials during the fabrication thereof including imaging multiple individual plies of a structure, whereby the locations and orientations of edge joints between adjacent courses of each ply are recorded, ascertaining mutual offsets in the locations of mutually parallel ones of the edge joints in the multiple individual plies and providing an output indication when at least one mutual offset of the edge joints is less than a predetermined minimum offset.

Preferably, the individual plies each extend in an X-Y plane and are stacked in a Z-direction, perpendicular to the X-Y plane of each of the individual plies and the mutual offsets are ascertained by comparing the location of each of the mutually parallel edge joints in the X-Y plane of each of the individual plies with the corresponding location of an edge joint which is mutually parallel thereto in the X-Y plane of another one of the individual plies.

In accordance with a preferred embodiment of the present invention the individual plies are non-planar and the mutual offsets are ascertained by comparing the location of each of the mutually parallel edge joints in each of the individual plies with the corresponding location of an edge joint which most closely corresponds thereto in location and orientation in another one of the individual plies.

In accordance with a preferred embodiment of the present invention the imaging multiple individual plies of a structure takes place during fabrication of the structure, at least between laying down of each of the multiple individual plies.

Preferably, the method for inspecting structures formed of composite materials during the fabrication thereof also includes providing a three-dimensional image file of the structure which enables ascertaining the mutual offsets in the locations of mutually parallel ones of the edge joints in the multiple individual plies.

There is also provided in accordance with another preferred embodiment of the present invention a method for inspecting structures formed of composite materials during the fabrication thereof including imaging multiple individual plies of a structure, whereby the locations and orientations of edge joints between adjacent courses of each ply are recorded and providing a three-dimensional image file of the structure which enables ascertaining mutual offsets in the locations of mutually parallel ones of the edge joints in the multiple individual plies.

Preferably, the individual plies each extend in an X-Y plane and are stacked in a Z-direction, perpendicular to the X-Y plane of each of the individual plies and the mutual offsets may be ascertained by comparing the location of each of the mutually parallel edge joints in the X-Y plane of each of the individual plies with the corresponding location of an edge joint which is mutually parallel thereto in the X-Y plane of another one of the individual plies.

In accordance with a preferred embodiment of the present invention the individual plies are non-planar and the mutual offsets may be ascertained by comparing the location of each of the mutually parallel edge joints in each of the individual plies with the corresponding location of an edge joint which most closely corresponds thereto in location and orientation in another one of the individual plies.

In accordance with a preferred embodiment of the present invention the imaging multiple individual plies of a structure takes place during fabrication of the structure at least between laying down of each of the multiple individual plies.

There is further provided in accordance with yet another preferred embodiment of the present invention a system for inspecting structures formed of composite materials during the fabrication thereof, the system including an imager operative to image multiple individual plies of a structure, whereby the locations and orientations of edge joints between adjacent courses of each ply are recorded, an offset analyzer operative to ascertain mutual offsets in the locations of mutually parallel ones of the edge joints in the multiple individual plies and a minimum offset threshold exceedance indicator providing an output indication when at least one mutual offset of the edge joints is less than a predetermined minimum offset.

Preferably, the individual plies each extend in an X-Y plane and are stacked in a Z-direction, perpendicular to the X-Y plane of each of the individual plies and the mutual offsets are ascertained by comparing the location of each of the mutually parallel edge joints in the X-Y plane of each of the individual plies with the corresponding location of an edge joint which is mutually parallel thereto in the X-Y plane of another one of the individual plies.

In accordance with a preferred embodiment of the present invention the individual plies are non-planar and the mutual offsets are ascertained by comparing the location of each of the mutually parallel edge joints in each of the individual plies with the corresponding location of an edge joint which most closely corresponds thereto in location and orientation in another one of the individual plies.

In accordance with a preferred embodiment of the present invention the imager is operative to image the multiple individual plies during fabrication of the structure at least between laying down of each of the multiple individual plies.

Preferably, the system for inspecting structures formed of composite materials during the fabrication thereof also includes an image file generator operative to provide a three-dimensional image file of the structure to said offset analyzer.

There is even further provided in accordance with still another preferred embodiment of the present invention a system for inspecting structures formed of composite materials during the fabrication thereof, the system including an imager operative to image multiple individual plies of a structure, whereby the locations and orientations of edge joints between adjacent courses of each ply are recorded, an offset analyzer operative to ascertain mutual offsets in the locations of mutually parallel ones of the edge joints in the multiple individual plies and an image file generator operative to provide a three-dimensional image file of the structure to the offset analyzer.

Preferably, the individual plies each extend in an X-Y plane and are stacked in a Z-direction, perpendicular to the X-Y plane of each of the individual plies and the mutual offsets may be ascertained by comparing the location of each of the mutually parallel edge joints in the X-Y plane of each of the individual plies with the corresponding location of an edge joint which is mutually parallel thereto in the X-Y plane of another one of the individual plies.

In accordance with a preferred embodiment of the present invention the individual plies are non-planar and the mutual offsets may be ascertained by comparing the location of each of the mutually parallel edge joints in each of the individual plies with the corresponding location of an edge joint which most closely corresponds thereto in location and orientation in another one of the individual plies.

In accordance with a preferred embodiment of the present invention the imager is operative to image the multiple individual plies during fabrication of the structure at least between laying down of each of the multiple individual plies.

BRIEF DESCRIPTION OF THE DRAWINGS

The present invention will be understood and appreciated more fully from the following detailed description, taken in conjunction with the drawings in which:

FIG. 5 is a simplified illustration of an output from the system of any of FIGS. 1-3 showing plies in a generally non-planar orientation.

DETAILED DESCRIPTION OF PREFERRED EMBODIMENTS

Figure 1:
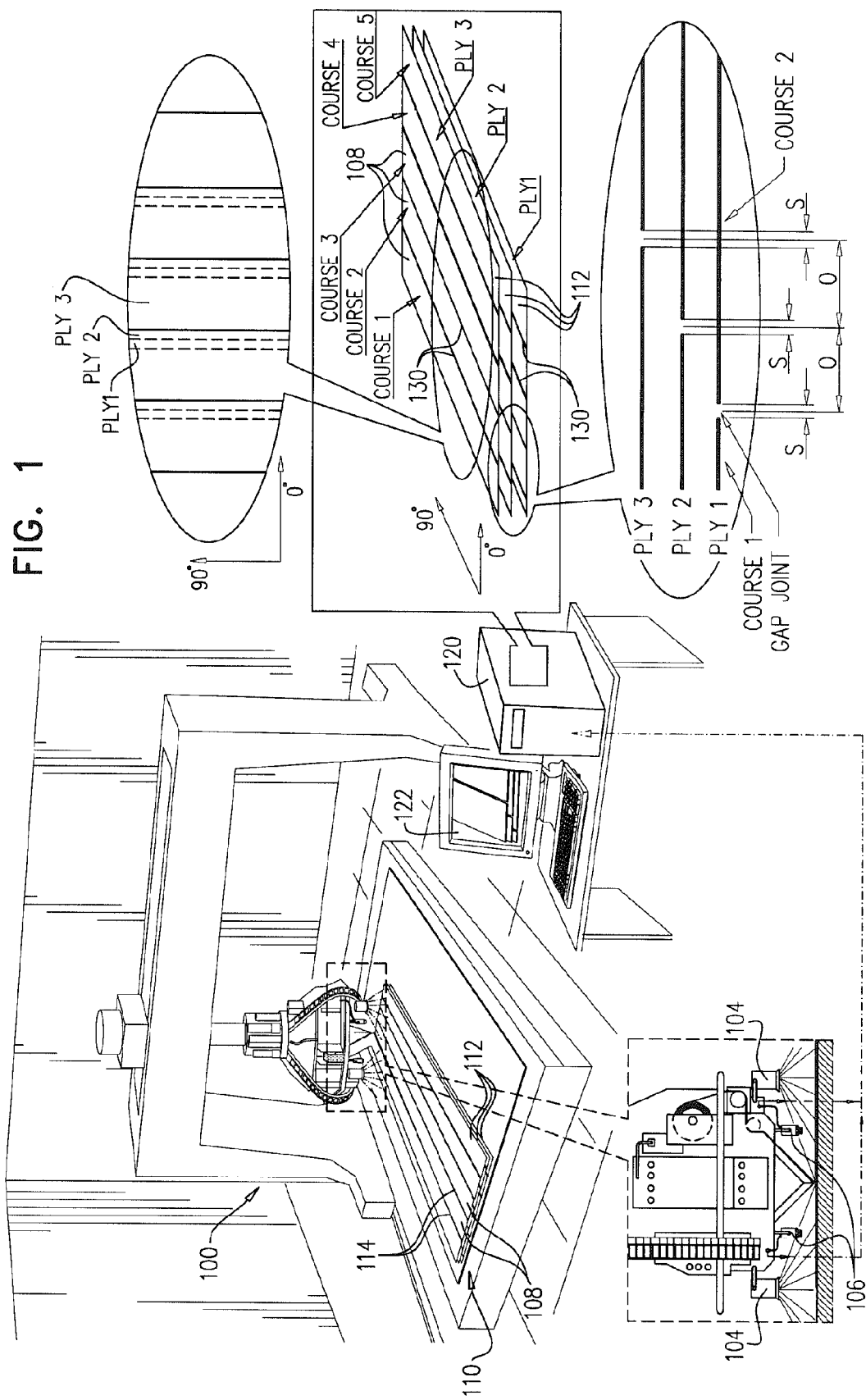
FIG. 1 is a simplified illustration of a system for inspecting structures formed of composite materials during the fabrication thereof, constructed and operative in accordance with a preferred embodiment of the present invention.

Reference is now made to FIG. 1, which is a simplified illustration of a system for inspecting structures formed of composite materials during the fabrication thereof, constructed and operative in accordance with a preferred embodiment of the present invention.

In the embodiment of FIG. 1, the system of the present invention is constructed and operative within the context of a Cincinnati Charger Tape Layer (CTL) machine 100, commercially available from Cincinnati Machine LLC of Hebron Ky., USA, preferably including a V5 head 102. It is appreciated that the system of the present invention is applicable to any suitable tape layup or fiber placement machine environment.

In accordance with a preferred embodiment of the present invention, multiple illuminators 104, preferably Nerlite® Machine Vision Lighting illuminators, such as dark field illuminators, DOAL® (Diffuse On-Axis Light) illuminators, or dome illuminators, commercially available from Microscan Systems, Inc., 700 SW 39$^{th}$ St., Renton, Wash. 98057, are mounted on head 102. Preferably multiple cameras 106, such as In-Sight Micro Series vision system cameras, commercially available from Cognex Corporation, One Vision Drive, Natick, Mass. 01760, are also mounted on head 102 to view multiple adjacent courses 108 of laid up tapes of a composite structure 110 in real time or near real time, thereby imaging multiple individual plies 112 of the composite structure, whereby the locations and orientations of edge joints 114 between adjacent courses 108 of each ply are preferably recorded. Edge joints 114 may be butt joints, at which edges of adjacent courses 108 touch each other, gap joints, at which edges of adjacent courses 108 are separated from each other by a separation S, or overlap joints at which edges of adjacent courses 108 overlap each other.

Outputs of cameras 106 are supplied to one or more computers 120 which preferably provide a three-dimensional image file of the composite structure. This three-dimensional image file enables ascertaining mutual offsets in the locations of mutually parallel ones of edge joints 114 in multiple individual plies 112. One or more display 122 shows a desired view of the composite structure, enabling an operator to view in real time or near real time the locations and orientations of edge joints 114 between adjacent courses 108 of each ply as the courses 108 are laid on the composite structure.

In the example illustrated in FIG. 1, all of the courses 108 in three illustrated plies 112 are mutually parallel and gap joints 130 are defined between adjacent parallel courses 108 in each ply 112. Typically in the aircraft industry there exist requirements as to the extent of separation between adjacent courses 108. In the illustrated example the requirements for gap joints 130 are that the adjacent parallel courses 108 be separated by a distance of between 0 and 2.54 mm. Overlaps of adjacent courses and separations between adjacent courses of more than 2.54 mm are considered to be defects and are detected by the system and methodology of the present invention.

Another important characteristic in the construction of composite structures is the offset between gap joints 130 of parallel plies 112, even when those plies are not adjacent each other in the composite structure. In the illustrated example, the offset between gap joints 130 of parallel plies 112 must be at least 12.7 mm. Offsets between gap joints 130 of parallel plies 112 less than 12.7 mm are considered to be defects and are detected by the system and methodology of the present invention.

In the context of the illustrated example, three plies 112, each including five adjacent courses 108, are shown. The separation between adjacent courses 108 at each gap joint 130 is designated as S and the offset between gap joints 130 of parallel plies 112 is designated as O. It is appreciated that the offset between gap joints 130 is normally equivalent to the offset between edge joints between adjacent courses.

In accordance with a preferred embodiment of the present invention, the computer 120 automatically provides an output indication when at least one mutual offset of the edge joints is less than a predetermined minimum offset.

Figure 2:
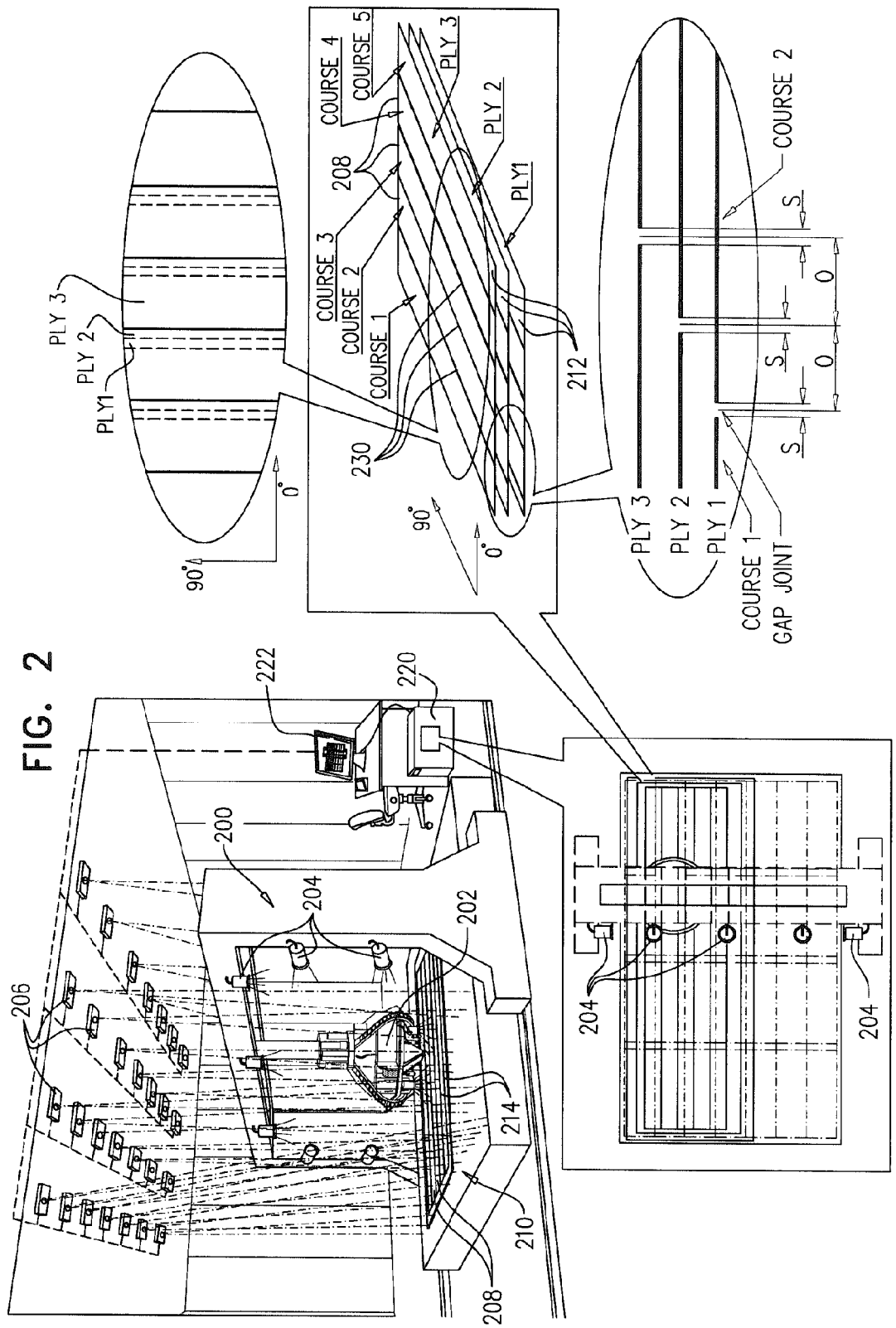
FIG. 2 is a simplified illustration of a system for inspecting structures formed of composite materials during the fabrication thereof, constructed and operative in accordance with another preferred embodiment of the present invention.

Reference is now made to FIG. 2, which is a simplified illustration of a system for inspecting structures formed of composite materials during the fabrication thereof, constructed and operative in accordance with another preferred embodiment of the present invention.

In the embodiment of FIG. 2, the system of the present invention is constructed and operative within the context of a Cincinnati Charger Tape Layer (CTL) machine 200, commercially available from Cincinnati Machine LLC of Hebron Ky., USA, preferably including a V5 head 202. It is appreciated that the system of the present invention is applicable to any suitable tape layup or fiber placement machine environment.

In accordance with a preferred embodiment of the present invention, multiple illuminators 204, preferably Nerlite® Machine Vision Lighting illuminators, such as dark field illuminators, DOAL® (Diffuse On-Axis Light) illuminators, or dome illuminators, commercially available from Microscan Systems, Inc., 700 SW 39th St., Renton, Wash. 98057, are mounted on the CTL machine 200. Preferably multiple cameras 206, such as In-Sight Micro Series vision system cameras, commercially available from Cognex Corporation, One Vision Drive, Natick, Mass. 01760, are mounted above the CTL machine 200, preferably on a ceiling, to view multiple adjacent courses 208 of laid up tapes of a composite structure 210 in real time or near real time, thereby imaging multiple individual plies 212 of the composite structure, whereby the locations and orientations of edge joints 214 between adjacent courses 208 of each ply are preferably recorded.

Outputs of cameras 206 are supplied to one or more computers 220 which preferably provide a three-dimensional image file of the composite structure. It is appreciated that whereas in the embodiment of FIG. 1, at any one time only a relatively small region of the composite structure 210 is viewed, in the embodiment of FIG. 2, nearly the entire composite structure 210 is viewed.

This three-dimensional image file enables ascertaining mutual offsets in the locations of mutually parallel ones of edge joints 214 in multiple individual plies 212. One or more display 222 shows a desired view of the composite structure, enabling an operator to view in real time or near real time the locations and orientations of edge joints 214 between adjacent courses 208 of each ply as the courses 208 are laid on the composite structure.

In the example illustrated in FIG. 2, all of the courses 208 in three illustrated plies 212 are mutually parallel and gap joints 230 are defined between adjacent parallel courses 208 in each ply 212. Typically in the aircraft industry there exist requirements as to the extent of separation between adjacent courses 208. In the illustrated example the requirements for gap joints 230 are that the adjacent parallel courses 208 be separated by a distance of between 0 and 2.54 mm. Overlaps of adjacent courses and separations between adjacent courses of more than 2.54 mm are considered to be defects and are detected by the system and methodology of the present invention.

Another important characteristic in the construction of composite structures is the offset between gap joints 230 of parallel plies 212, even when those plies are not adjacent each other in the composite structure. In the illustrated example, the offset between gap joints 230 of parallel plies 212 must be at least 12.7 mm. Offsets between gap joints 230 of parallel plies 212 less than 12.7 mm are considered to be defects and are detected by the system and methodology of the present invention.

In the context of the illustrated example, three plies 212, each including five adjacent courses 208, are shown. The separation between adjacent courses 208 at each gap joint 230 is designated as S and the offset between gap joints of parallel plies is designated as O. It is appreciated that the offset between gap joints is normally equivalent to the offset between edge joints between adjacent courses.

In accordance with a preferred embodiment of the present invention, the computer 220 automatically provides an output indication when at least one mutual offset of the edge joints is less than a predetermined minimum offset.

Figure 3:
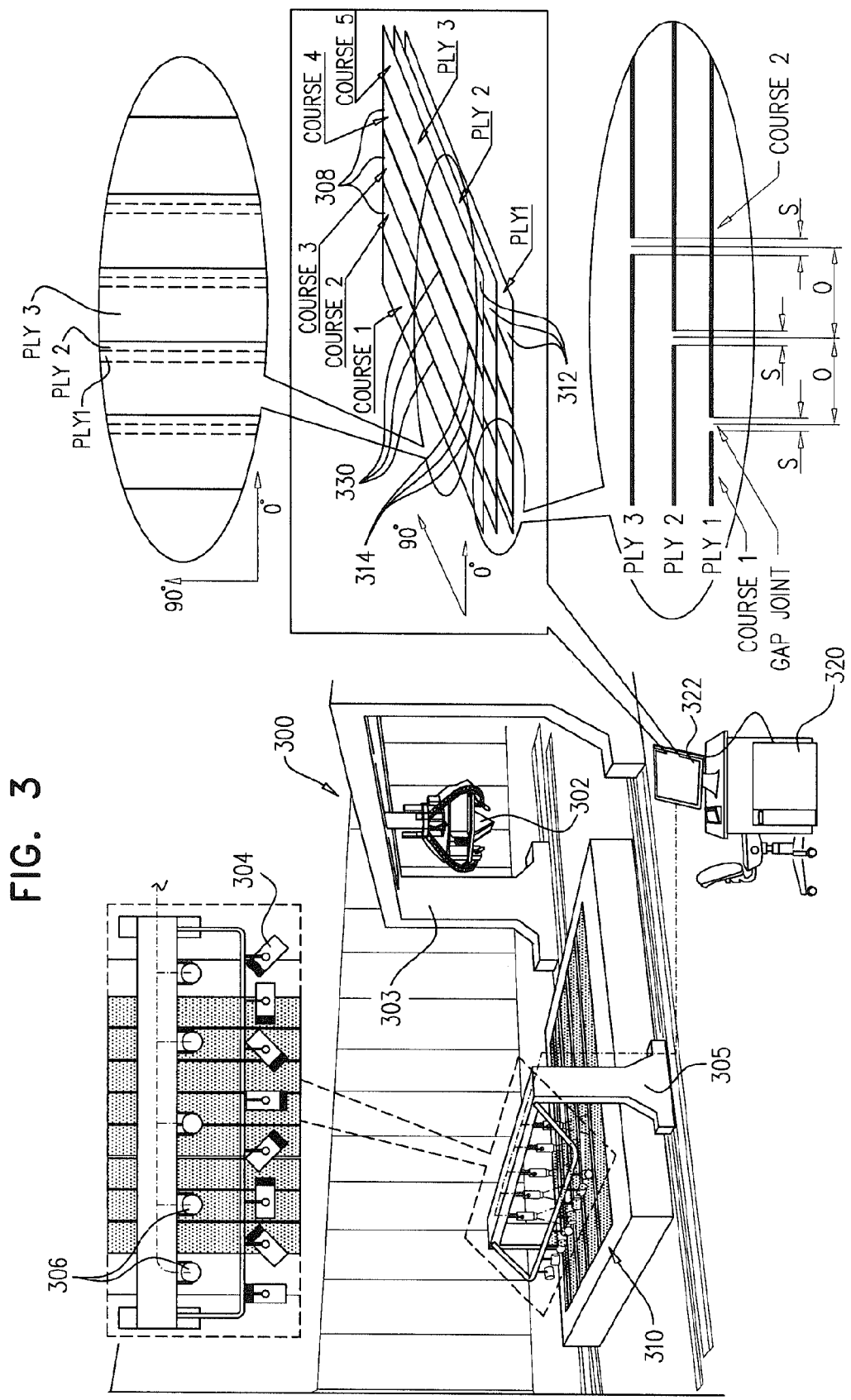
FIG. 3 is a simplified illustration of a system for inspecting structures formed of composite materials during the fabrication thereof, constructed and operative in accordance with a yet another preferred embodiment of the present invention.

Reference is now made to FIG. 3, which is a simplified illustration of a system for inspecting structures formed of composite materials during the fabrication thereof, constructed and operative in accordance with yet another preferred embodiment of the present invention.

In the embodiment of FIG. 3, the system of the present invention is shown alongside a Cincinnati Charger Tape Layer (CTL) machine 300, commercially available from Cincinnati Machine LLC of Hebron Ky., USA, preferably including a V5 head 302. In this embodiment, the operation of the system of the present invention is generally independent of the operation of the CTL machine 300 other than to the extent that the gantry 303 of the CTL machine must be out of the way and stationary during the imaging operation of the system of the present invention. It is appreciated that the system of the present invention is useful with any suitable tape layup or fiber placement machine environment.

In accordance with a preferred embodiment of the present invention, multiple illuminators 304, preferably Nerlite® Machine Vision Lighting illuminators, such as dark field illuminators, DOAL® (Diffuse On-Axis Light) illuminators, or dome illuminators, commercially available from Microscan Systems, Inc., 700 SW $39^{th}$ St., Renton, Wash. 98057, are mounted on a special purpose gantry 305. Preferably multiple cameras 306, such as In-Sight Micro Series vision system cameras, commercially available from Cognex Corporation, One Vision Drive, Natick, Mass. 01760, are also mounted on gantry 305 to view multiple adjacent courses 308 of laid up tapes of a composite structure 310 in real time or near real time, preferably after each ply 312 is laid down, thereby imaging multiple individual plies 312 of the composite structure, whereby the locations and orientations of edge joints 314 between adjacent courses 308 of each ply are preferably recorded.

Outputs of cameras 306 are supplied to one or more computers 320 which preferably provide a three-dimensional image file of the composite structure. This three-dimensional image file enables ascertaining mutual offsets in the locations of mutually parallel ones of edge joints 314 in multiple individual plies 312. One or more display 322 shows a desired view of the composite structure, enabling an operator to view in real time or near real time the locations and orientations of edge joints 314 between adjacent courses 308 of each ply as the courses 308 are laid on the composite structure.

In the example illustrated in FIG. 3, all of the courses 308 in three illustrated plies 312 are mutually parallel and gap joints 330 are defined between adjacent parallel courses 308 in each ply 312. Typically in the aircraft industry there exist requirements as to the extent of separation between adjacent courses 308. In the illustrated example the requirements for gap joints 330 are that the adjacent parallel courses 308 be separated by a distance of between 0 and 2.54 mm. Overlaps of adjacent courses and separations between adjacent courses of more than 2.54 mm are considered to be defects and are detected by the system and methodology of the present invention.

Another important characteristic in the construction of composite structures is the offset between gap joints 330 of parallel plies 312, even when those plies are not adjacent each other in the composite structure. In the illustrated example, the offset between gap joints 330 of parallel plies 312 must be at least 12.7 mm. Offsets between gap joints 330 of parallel plies 312 less than 12.7 mm are considered to be defects and are detected by the system and methodology of the present invention.

In the context of the illustrated example, three plies 312, each including five adjacent courses 308, are shown. The separation between adjacent courses 308 at each gap joint 330 is designated as S and the offset between gap joints of parallel plies is designated as O. It is appreciated that the offset between gap joints is normally equivalent to the offset between edge joints between adjacent courses.

In accordance with a preferred embodiment of the present invention, the computer 320 automatically provides an output indication when at least one mutual offset of the edge joints is less than a predetermined minimum offset.

Figure 4:
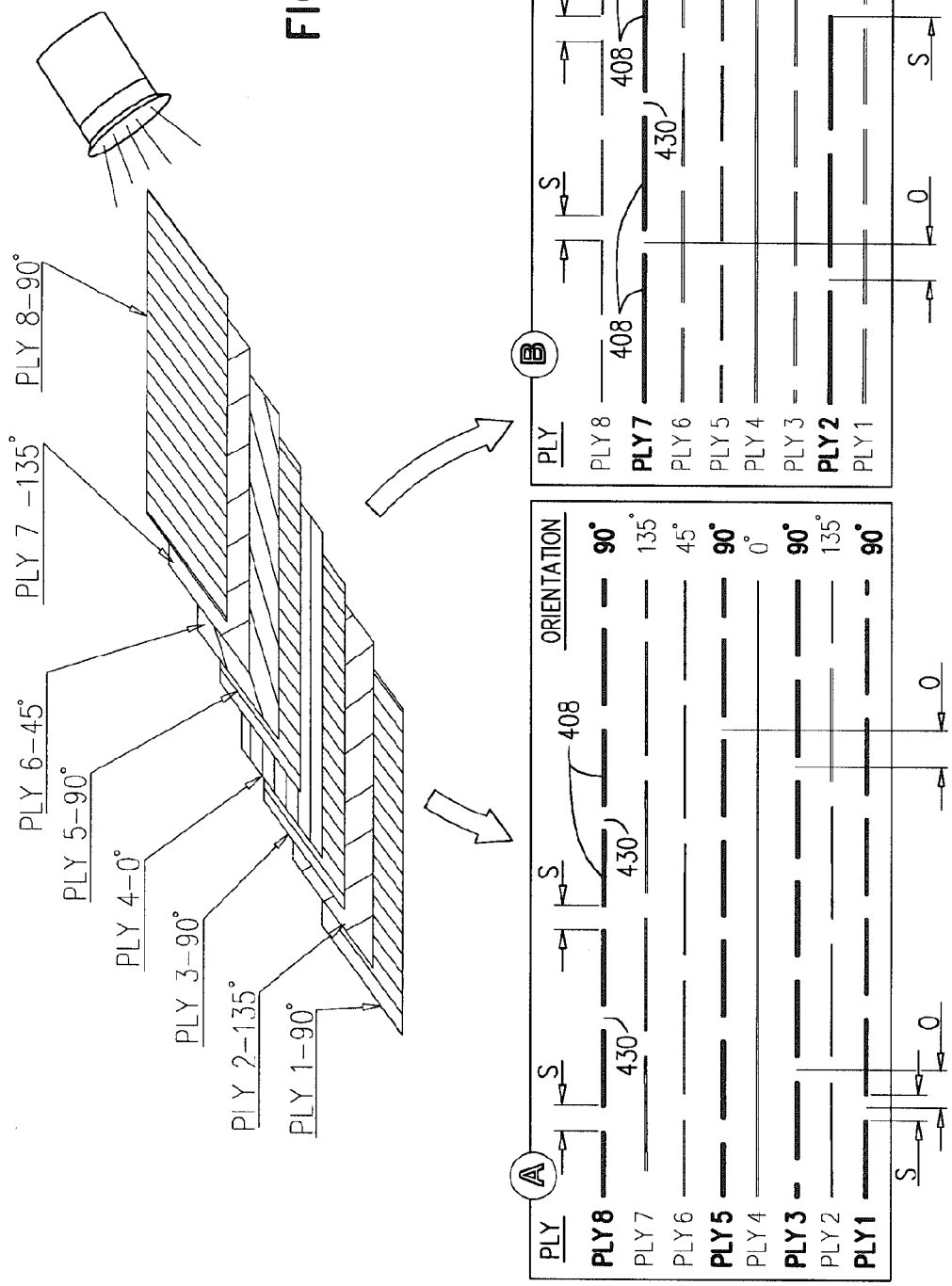
FIG. 4 is a simplified illustration of an output from the system of any of FIGS. 1-3 showing plies in a generally planar orientation.

Reference is now made to FIG. 4, which is a simplified illustration of an output from the system of any of FIGS. 1-3 showing plies in a generally planar orientation. In the example shown in FIG. 4, the courses that make up plies 1, 3, 5 and 8 are mutually parallel; the courses that make up plies 2 and 7 are mutually parallel, but are angled relative to the courses that make up plies 1, 3, 5 and 8, and the courses that make up plies 4 and 6 are each not parallel to courses in any of the other plies in the illustrated composite article.

FIG. 4 illustrates, at A, a cross-sectional cut taken from a three dimensional map automatically produced by the system of the present invention which clearly shows and emphasizes both the separation, designated S, between adjacent courses 408 at each gap joint 430 in mutually parallel plies 1, 3, 5 and 8, and the offset, designated O, between gap joints 430 of mutually parallel plies 1, 3, 5 and 8.

FIG. 4 illustrates, at B, a cross-sectional cut taken from a three dimensional map automatically produced by the system of the present invention which clearly shows and emphasizes both the separation, designated S, between adjacent courses 408 at each gap joint 430 in mutually parallel plies 2 & 7, and the offset, designated O, between gap joints 430 of mutually parallel plies 2 & 7.

Reference is now made to FIG. 5, which is a simplified illustration of an output from the system of any of FIGS. 1-3 showing plies in a generally non-planar orientation. In the example shown in FIG. 5, the courses 508 that make up plies 1, 3, 5 and 8 are mutually parallel; the courses that make up plies 2 and 7 are mutually parallel but are angled relative to the courses that make up plies 1, 3, 5 and 8 and the courses that make up plies 4 and 6 are each not parallel to courses in any of the other plies in the illustrated composite article.

FIG. 5 illustrates, at A, a cross-sectional cut taken from a three dimensional map automatically produced by the system of the present invention which clearly shows and emphasizes both the separation, designated S, between adjacent courses 508 at each gap joint 530 in mutually parallel plies 1, 3, 5 and 8, and the offset, designated O, between gap joints 530 of mutually parallel plies 1, 3, 5 and 8.

FIG. 5 illustrates, at B, a cross-sectional cut taken from a three dimensional map automatically produced by the system of the present invention which clearly shows and emphasizes both the separation, designated S, between adjacent courses 508 at each gap joint 530 in mutually parallel plies 2 & 7, and the offset, designated O, between gap joints 530 of mutually parallel plies 2 & 7.

The invention claimed is:

1. A method for inspecting structures formed of composite materials during the fabrication thereof comprising:
    imaging multiple individual plies of a structure, whereby the locations and orientations of edge joints between adjacent courses of each ply are recorded;
    ascertaining mutual offsets in the locations of mutually parallel ones of said edge joints in said multiple individual plies; and
    providing an output indication when at least one mutual offset of said edge joints is less than a predetermined minimum offset.

2. A method for inspecting structures formed of composite materials during the fabrication thereof according to claim 1 and wherein:
    said individual plies each extend in an X-Y plane and are stacked in a Z-direction, perpendicular to the X-Y plane of each of said individual plies; and
    said mutual offsets are ascertained by comparing the location of each of said mutually parallel edge joints in the X-Y plane of each of said individual plies with the corresponding location of an edge joint which is mutually parallel thereto in the X-Y plane of another one of said individual plies.

3. A method for inspecting structures formed of composite materials during the fabrication thereof according to claim 1 and wherein:
    said individual plies are non-planar; and
    said mutual offsets are ascertained by comparing the location of each of said mutually parallel edge joints in each of said individual plies with the corresponding location of an edge joint which most closely corresponds thereto in location and orientation in another one of said individual plies.

4. A method for inspecting structures formed of composite materials during the fabrication thereof according to claim 1 and wherein said imaging multiple individual plies of a structure takes place during fabrication of said structure, at least between laying down of each of said multiple individual plies.

5. A method for inspecting structures formed of composite materials during the fabrication thereof according to claim 1 and also comprising:
    providing a three-dimensional image file of said structure which enables ascertaining the mutual offsets in the locations of mutually parallel ones of said edge joints in said multiple individual plies.

6. A method for inspecting structures formed of composite materials during the fabrication thereof comprising:
    imaging multiple individual plies of a structure, whereby the locations and orientations of edge joints between adjacent courses of each ply are recorded, said individual plies each extending in an X-Y plane and being stacked in a Z-direction, perpendicular to the X-Y plane of each of said individual plies;
    providing a three-dimensional image file of said structure which enables ascertaining mutual offsets in the locations of mutually parallel ones of said edge joints in said multiple individual plies; and
    ascertaining said mutual offsets by comparing the location of each of said mutually parallel edge joints in the X-Y plane of each of said individual plies with the corresponding location of an edge joint which is mutually parallel thereto in the X-Y plane of another one of said individual plies.

7. A method for inspecting structures formed of composite materials during the fabrication thereof according to claim 6 and wherein said imaging multiple individual plies of a structure takes place during fabrication of said structure at least between laying down of each of said multiple individual plies.

8. A method for inspecting structures formed of composite materials during the fabrication thereof comprising:
    imaging multiple individual plies of a structure, whereby the locations and orientations of edge joints between adjacent courses of each ply are recorded, said individual plies being non-planar;
    providing a three-dimensional image file of said structure which enables ascertaining mutual offsets in the locations of mutually parallel ones of said edge joints in said multiple individual plies; and ascertaining said mutual offsets by comparing the location of each of said mutually parallel edge joints in each of said individual plies with the corresponding location of an edge joint which most closely corresponds thereto in location and orientation in another one of said individual plies.

9. A method for inspecting structures formed of composite materials during the fabrication thereof according to claim 8 and wherein said imaging multiple individual plies of a structure takes place during fabrication of said structure at least between laying down of each of said multiple individual plies.

10. A system for inspecting structures formed of composite materials during the fabrication thereof, the system comprising:
- an imager operative to image multiple individual plies of a structure, whereby the locations and orientations of edge joints between adjacent courses of each ply are recorded;
- an offset analyzer operative to ascertain mutual offsets in the locations of mutually parallel ones of said edge joints in said multiple individual plies; and
- a minimum offset threshold exceedance indicator providing an output indication when at least one mutual offset of said edge joints is less than a predetermined minimum offset.

11. A system for inspecting structures formed of composite materials during the fabrication thereof according to claim 10 and wherein:
- said individual plies each extend in an X-Y plane and are stacked in a Z-direction, perpendicular to the X-Y plane of each of said individual plies; and
- said mutual offsets are ascertained by comparing the location of each of said mutually parallel edge joints in the X-Y plane of each of said individual plies with the corresponding location of an edge joint which is mutually parallel thereto in the X-Y plane of another one of said individual plies.

12. A system for inspecting structures formed of composite materials during the fabrication thereof according to claim 10 and wherein:
- said individual plies are non-planar; and
- said mutual offsets are ascertained by comparing the location of each of said mutually parallel edge joints in each of said individual plies with the corresponding location of an edge joint which most closely corresponds thereto in location and orientation in another one of said individual plies.

13. A system for inspecting structures formed of composite materials during the fabrication thereof according to claim 10 and wherein said imager is operative to image said multiple individual plies during fabrication of said structure at least between laying down of each of said multiple individual plies.

14. A system for inspecting structures formed of composite materials during the fabrication thereof according to claim 10 and also comprising:
- an image file generator operative to provide a three-dimensional image file of said structure to said offset analyzer.

15. A system for inspecting structures formed of composite materials during the fabrication thereof, the system comprising:
- an imager operative to image multiple individual plies of a structure, whereby the locations and orientations of edge joints between adjacent courses of each ply are recorded, said individual plies each extending in an X-Y plane and being stacked in a Z-direction, perpendicular to the X-Y plane of each of said individual plies;
- an offset analyzer operative to ascertain mutual offsets in the locations of mutually parallel ones of said edge joints in said multiple individual plies by comparing the location of each of said mutually parallel edge joints in the X-Y plane of each of said individual plies with the corresponding location of an edge joint which is mutually parallel thereto in the X-Y plane of another one of said individual plies; and
- an image file generator operative to provide a three-dimensional image file of said structure to said offset analyzer.

16. A system for inspecting structures formed of composite materials during the fabrication thereof according to claim 15 and wherein said imager is operative to image said multiple individual plies during fabrication of said structure at least between laying down of each of said multiple individual plies.

17. A system for inspecting structures formed of composite materials during the fabrication thereof the system comprising:
- an imager operative to image multiple individual plies of a structure, whereby the locations and orientations of edge joints between adjacent courses of each ply are recorded, said individual plies being non-planar;
- an offset analyzer operative to ascertain mutual offsets in the locations of mutually parallel ones of said edge joints in said multiple individual plies by comparing the location of each of said mutually parallel edge joints in each of said individual plies with the corresponding location of an edge joint which most closely corresponds thereto in location and orientation in another one of said individual plies; and
- an image file generator operative to provide a three-dimensional image file of said structure to said offset analyzer.

18. A system for inspecting structures formed of composite materials during the fabrication thereof according to claim 17 and wherein said imager is operative to image said multiple individual plies during fabrication of said structure at least between laying down of each of said multiple individual plies.

* * * * *